US007396946B2

(12) United States Patent
Ueno

(10) Patent No.: US 7,396,946 B2
(45) Date of Patent: Jul. 8, 2008

(54) COMPOUND FOR TREATMENT OF EXTERNAL SECRETION DISORDERS

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 193 days.

(21) Appl. No.: 10/994,364

(22) Filed: Nov. 23, 2004

(65) Prior Publication Data

US 2005/0090556 A1    Apr. 28, 2005

Related U.S. Application Data

(62) Division of application No. 10/377,743, filed on Mar. 4, 2003, now abandoned, which is a division of application No. 09/615,703, filed on Jul. 13, 2000, now Pat. No. 6,566,398.

(60) Provisional application No. 60/143,627, filed on Jul. 14, 1999.

(51) Int. Cl.
| | |
|---|---|
| *A61K 31/20* | (2006.01) |
| *C07G 59/205* | (2006.01) |
| *C07C 61/06* | (2006.01) |
| *C07C 405/00* | (2006.01) |
| *C07G 59/21* | (2006.01) |
| *C07G 59/215* | (2006.01) |
| *C07C 61/08* | (2006.01) |
| *C07C 61/20* | (2006.01) |
| *C07C 61/22* | (2006.01) |

(52) U.S. Cl. ............... 554/118; 514/557; 514/559; 554/117; 554/119; 562/503

(58) Field of Classification Search ........... 514/557, 514/559; 562/503
See application file for complete search history.

(56) References Cited

U.S. PATENT DOCUMENTS

| | | | |
|---|---|---|---|
| 4,388,324 | A | 6/1983 | Horribin |
| 4,535,093 | A | 8/1985 | Horribin |
| 5,164,415 | A | 11/1992 | Ueno |
| 5,212,324 | A | 5/1993 | Ueno |
| 5,369,127 | A | 11/1994 | Burk et al. |
| 5,686,487 | A * | 11/1997 | Ueno .................. 514/530 |
| 5,696,166 | A | 12/1997 | Yanni et al. |
| 6,211,197 | B1 | 4/2001 | Belley et al. |

FOREIGN PATENT DOCUMENTS

| | | |
|---|---|---|
| EP | 0284810 | 5/1988 |
| EP | 0 308 135 | 3/1989 |
| EP | 0453127 A2 | 10/1991 |
| EP | 0 503 887 A2 | 9/1992 |
| EP | 0690049 A2 | 1/1996 |
| HU | P9502004 A | 4/1994 |
| JP | 2-32055 A | 2/1990 |
| WO | WO 94/24121 | 10/1994 |
| WO | WO 00/38663 | 7/2000 |
| WO | WO 00/38690 | 7/2000 |

OTHER PUBLICATIONS

U.S. Appl. No. 11/399,495, filed Aug. 2006, Ueno, Ryuji.*
U.S. Appl. No. 11/366,413, filed Mar. 2006, Ueno, Ryuji.*
Hall et al. "Structure-Activity Relationships in a Series of 11-deoxy Prostaglandins" Prostaglandins (1976) vol. 11, No. 3, pp. 573-587.*
D. F. Horrobin et al.; Sjogren's Syndrome and the Sicca Syndrome: The Role of Postaglandin E1 Deficiency. Treatment with Essential Fatty Acids and Vitamin C; Medical Hypotheses; vol. 6, pp. 225-232, 1980.
C. Pholpramool; Secretory Effect of Prostaglandins on the Rabbit Lacrimal Gland In Vivo; Prostaglandins and Medicine, vol. 3, pp. 185-192, 1979.
Norio Taira and Susumu Satoh; Differential Effects of Tetrodotoxin on the Sialogenous and Vasodilator Actions of Prostaglandin $E_2$ in the Dog Salivary Gland; Life Sciences, vol. 15, pp. 987-993, 1974.
Norio Taira and Susumu Satoh; Prostaglandin $F_{2\alpha}$ as a Potent Excitant of the Parasympathetic Postganglionic Neurons of the Dog Salivary Gland, Life Sciences, vol. 13, pp. 501-506, 1973.
Russian Official Action, Application No. 2002103597/15(004431), Application filing date: Jul. 13, 2000, Application No. PCT/JP 00/04696, Appln. NoEA, Applicant(s): Sucampo AG, CH.
Follmann et al. Klinische Monatsblatter Fur Augenheilkunde, (Jan. 1980) 176(1) 147-52. (in German, English Abstract).
N. Taira et al., "Mode of actions of prostaglandin E2, Flaipha and F2 alpha in the dog salivary gland", INT Union Pharmacol Proceedings of the International Congress of Pharmacology 1977, p. 159 XP001011501.
N. Taira et al. "Prostaglandin F2alpha as a potent excitant of the parasympathetic postganglionic neuron of the dog salivary gland" Life Sciences, vol. 13., No. 5,1973, pp. 501-506, XP001011455.
N. Taira et al. "Differential effects of tetrodotoxin on the sialogenous and vasodilator action of prostaglandin E2 in the dog salivary gland" Life Sciences, vol. 15, No. 5,1974, pp. 987-993, XP001011500.
C. Pholpramoo et aL "Secretory effect of prostaglainds on the rabbit lacrimal gland in vied" Prostaglandin and medicine, vol. 3, No. 3,1979, pp. 185-192, XP001011481.
F.M.C. De Farias "Prostaglandin analogues the synthesis of new prostanoids from natural safrole" Quimica Nova, vol. 7, No. 2,1984, pp. 111-112, XP001011499.
R.A. Hahn, et al. "Salivation induced by prostaglandin F2ac and modification of the response by atropine and physostigmine" Br. J. Pharinaco (1972), 44, 527-533.
R.A. Hahn, et aL "Further observations on the interaction of prostaglandin Fzac with cholinergic mechanisms in canine salivary glands" European Journal of Pharmacology 25 (1974) vol. 25, No. 3 279-286.

(Continued)

*Primary Examiner*—Shaojia Anna Jiang
*Assistant Examiner*—Eric S Olson
(74) *Attorney, Agent, or Firm*—Sughrue Mion, PLLC

(57) ABSTRACT

Disclosed is a method for treatment of external secretion disorders, which comprises administering a fatty 5 acid derivative to a subject in need of said treatment. The method of the present invention is useful for treatment of at least one condition selected from hypolacrimation including disorder of basal tear secretion, dry-eye syndrome, hyposalivation and dry-mouth syndrome.

2 Claims, No Drawings

OTHER PUBLICATIONS

N. Taira et al. "Differential block by 1-hyoscyamine of the salivary and vascular-response of the dog msndi'bular gland to prostaglandin F2ac" Life Sciences vol. 17, No. 12: 1869-1876(1975).

J.H. Yu, et al. Prostaglandin E1 induced salivary secretion; Experientica 38(1982), 1077-1078.

B.H. Kim "Studies on the effects of prostaglandin and biadykinin on salivary flow, blood flow and cyclic Nucleotide contents in the submaxillary gland of cat" Journal of Osaka Dental University vol. 16, No. 1: 52-66 (1982).

M. Rodrigues, et al. "Prostaglandin as biochemical markers of radiation injury to the salivary glands after iodine-131 therapy" European Journal of Nuclear Medicine vol. 25, No. 3:265-269 (1998).

S.M.M. Katrim, et at "Effect of Topical prostaglandin on Nasal, Patency In Man" Prostaglandin vol. 15, No. 3:457-462, 1978.

S.M.M. Karim, et al. "Effect of 17 Phenyl PGF2a On Nasal Patency In Man", Prostaglandin and Medicine vol. 3, No. 1: 33-37, 1979.

C. Pholpramool "Secretory Effect of Prostaglandin On the Rabbit Lacrimal Gland In Vivo" Prostaglandin and Medicine 3:185-192, 1979.

D.F. Horrobin, et al. "Sjogren's Syndrome and theSicca Syndrome: The Role of Prostaglandin E, Deficiency. Treatment with Essential Fatty Acids and Vitamin C" Medical Hypotheses, 6:225-232,1980.

Robert J. R. McKendry "Treatment of Sjogren's Syndrome with Essential Fatty Acids, Pyridoxine and Vitamin C" Prostaglandin Leukotriences and Medicine vol. 8, No. 4:403-408, 1982.

C. Pholpramool, et aL "Evidence for the Requirement of Sympathetic Activity in the POE,—Induced Iscrimal Secretion in Rabbits" Arch Int. Phamracodyn 265:128-137 (1983).

R Manthorpe, et aL "Primary Sjogren's syndrome treated with Efamol/Efavit. A double blind cross-over investigation" Rheumatol Int. (1984) 4:165-167.

P. Aragona, et al. "Effects of a Stable Analogue of POE2 (11-deoxy-13,14-didehydro-16 (s)-methylester methyl POE2: FCE 20700) on the Secretory Processes of Conjunctiva) Goblet Cells of Rabbit" Exp. Eye Res. vol. 45, No. 5: 647-654,1987.

Yasumasa Goh, et al. "Ocular Hypotensive and Adverse Effects After Topical Application of Prostaglandin Analogue, 5-1033, In Animate: A Comparative Study with OF-021 and PHXA34" Japan L Ophthslmnl 38:215-227,1994.

Hirosbi Toshida, et aL "Effects on Tear Secretion of Isopropyl Unoprostone Eye Drops in Rabbits" Folia Ophthalmol Japan 47:1323-1328 (1996.

* cited by examiner

COMPOUND FOR TREATMENT OF EXTERNAL SECRETION DISORDERS

CROSS REFERENCE TO RELATED APPLICATIONS

This is a divisional of application Ser. No. 10/377,743 filed Mar. 4, 2003, now abandoned which is a divisional application of 09/615,703 filed Jul. 13, 2000, now U.S. Pat. No. 6,566,398 which claims benefit of Provisional Application No. 60/143,627 filed Jul. 14, 1999.

TECHNICAL FIELD

The present invention relates to a method for treatment of external secretion disorders, particularly, to a method for treatment of hypolacrimation including dry-eye syndrome and hyposalivation including dry-mouth syndrome.

BACKGROUND ART

External secretions are discharges that are discharged directly from the exocrine glandular cells or through the excretory ducts or the like onto the body surface or into a lumen. Tear and saliva are the typical external secretions and secretions from the nasal or the respiratory tract mucosa, secretions from the stomach or the intestine, discharges from the vagina, perspiration, etc are also included. Conditions resulting from external secretion disorders include dryness of various parts of the body such as "dry-eye syndrome" (xerophthalmia), "dry-mouth syndrome" (xerostomia), "dry nose syndrome" (xeromycteria), "dry-skin syndrome" (xeroderma), and "dry-vagina syndrome" (symptom of vaginal dryness); and chronic pancreatitis, chronic gastritis, and chronic bronchitis due to depression of the external secretion.

"Sjögren's syndrome", an autoimmune disease, is one of the variety of known and unknown etiologic factors which may responsible for external secretion disorders. Sjögren's syndrome is characterized by dryness condition due to infiltration of inflammatory cells into the acinus of the exocrine gland and around the excretory duct, which results in destruction and atrophy of the acinus and the epithelial cells of the duct. Typical symptoms include eye and mouth dryness, as well as dryness of skin, nose, throat, bronchia, vulva, and vagina. For example, dryness of the respiratory tract may induce infections in the lung and sometimes may cause serious disorders such as pneumonia that may lead to death. The other major etiology is aging. Although the external secretion disorders may cause serious diseases as mentioned above, merely symptomatic treatment methods such as artificial hydration have been available for the disorders so far. Therefore, development of a fundamental treatment to improve the depressed external secretion has been desired.

One of the diseases caused by the external secretion disorders, and which has been a current keen interest in the medical and pharmaceutical field, is hypolacrimation including dry-eye syndrome.

Dry-eye syndrome is defined as a condition with decrease or change in quality of tear irrespective of the presence or absence of corneal and conjunctival lesion (Yamada et al., GANKI 43, 1289-1293(1992)). It include dry-eye conditions found in the patients of hypolacrimation, alacrima, xerophthalmia, Sjögren's syndrome, keratoconjunctivitis sicca, Stevens-Johnson syndrome, ocular pemphigoid, blepharitis marginal, and diabetes, etc.; post-cataract surgery dry eye; allergic conjunctivitis-associated dry eye; and age-related dry-eye syndrome. Further, dry-eye also includes the conditions found in hypolacrimation patients induced by long time visual display terminal (VDT) operations, room dryness due to air-conditioning and the like.

There are various etiologies of the dry-eye syndrome, including the above described and that have unidentified. However, at present, only palliative treatments for the dry-eye syndrome including administering an artificial tear solution to increase the quantity of tear retained within the conjunctival sac thereby relieve the subjective symptoms or protecting the eyes from dryness have been available. It has been desired to provide compositions which is capable of bringing satisfactory treatment, including improvement of hypolacrimation.

The tear secretion is classified into basal tear secretion and reflex tear secretion. Basal tear secretion is that under ordinary conditions with the eyelid open, and is considered being mainly from the accessory lacrimal glands e.g. Kraus gland and Wolfring gland. On the other hand, reflux tear secretion is tear secretion in response to some stimulation in the keratoconjunctival surface, nasal mucosa, or the like, or that accompanied with mental changes such as grief or joy. It is considered to be from the main lacrimal gland. Considering the symptoms of the dry-eye syndrome, improvement of the decreased basal tear secretion, i.e. tear secretion under ordinary conditions with the eyelid open, is particularly important.

Further, the diseases caused by external secretion disorders also include hyposalivation, and it may be sometimes accompanied by dry-mouth syndrome (xerostomia). In dry-mouth patients, the decreased amount of saliva secretion causes dryness of the lip and oral cavity and may induce thirst feeling, xerosis of tunica mucosa oris, urtication, dysmaesesis, and dyspepsia. Also, in the patients with dry-mouth syndrome, foods are likely to remain inside the mouth and may result in dental caries.

There are a variety of etiologic factors which are responsible for the dry-mouth syndrome. For example, systemic factors include febrile disease, dehydration, endocrinopathy (myxedema, Basedow's disease, diabetes insipidus, etc.) metabolic disorders (diabetes, uremia, liver cirrhosis, etc.) deficiency of Vitamin-A, B, autoimmune disease (Sjögren's syndrome, progressive scleroderma, etc.) anemia, bleeding, aging, various medicaments (sedatives, parasympatholytic drugs, antihistamines, etc.). Local factors include sialadenitis, atrophy of salivary gland, sequela of radio therapy, and malformation (ectodermal dysplasia, etc.)

As described above, there are a variety of known and unknown etiologic factors responsible for the dry-mouth syndrome. However, at present, only palliative treatments for the dry-mouth syndrome such as drinking liquid all day long little by little, chewing gum or the like, and using artificial saliva have been available. It has been desired to provide a composition which is capable of bringing fundamental treatment such that to improve the decreased saliva secretion.

Generally, a healthy normal person discharges 1 to 1.5 litter of saliva a day through a pair of left and right major salivary glands (including parotid gland, submandibular gland, and sublingual gland) and minor salivary glands (including labial glands, lingual glands, palatine glands, and buccal glands). Saliva is discharged in response to a stimulant which may harm body to dilute the same or to maintain the physiological pH value, as well as helping mastication and deglutition of foods. Further, saliva dissolves foods thereby makes a person taste them and helps him smoothly utter words by keeping a wet state inside the mouth. There are two types of saliva: one is the continuous type that keeps on discharging a small amount without a particular stimulant and the other is the reflective type that is discharged in response to stimulation by food, gnatho-movement, taste and the like. In any case, saliva secretion is one of the essential physiological functions and hence improving the decreased saliva secretion is particularly important in treating the dry-mouth syndrome.

In the past, some of fatty acids had been rated as essential, and enough amount of them were required to be taken from the nutrient point of view. Recently, bioactivities of a variety of fatty acids have been studied and the activities of linoleic acid, arachidonic acid, α-linolenic acid, eicosapentaenoic acid (EPA), and docosahexaenoic acid (DHA) have attracted the attention linoleic acid is converted through di-homo-γ-linolenic acid to arachidonic acid; α-linolenic acid is converted through eicosapentaenoic acid (EPA) to docosahexaenoic acid (DHA); di-homo-γ-linolenic acid is converted into type 1 prostaglandin ($PG_1$), arachidonic acid is converted into type 2 prostaglandin ($PG_2$) or type 4 leukotriene ($LT_4$), and eicosapentaenoic acid is converted into type 3 prostaglandin or type 5 leukotriene ($LT_5$) in vivo respectively.

Prostaglandins (hereinafter, referred to as PG(s)) are members of class of organic carboxylic acids, which are contained in tissues or organs of human or most other mammalian, and exhibit a wide range of physiological activity. PGs found in nature (primary PGs) generally have a prostanoic acid skeleton as shown in the formula (A):

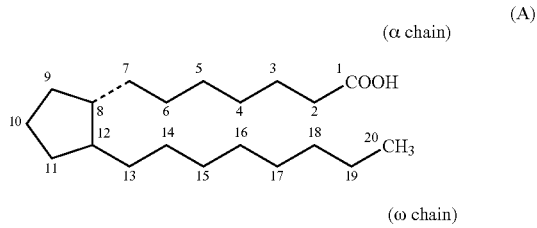

On the other hand, some of synthetic analogues have a modified skeleton. The primary PGs are classified to PGAs, PGBs, PGCs, PGDs, PGES, PGFs, PGGs, PGHs, PGIs and PGJs according to the structure of the five-membered ring moiety, and further classified into the following three types by the number and position of the unsaturated bond at the carbon chain moiety:
subscript 1: 13,14-unsaturated-15-OH
subscript 2: 5,6- and 13,14-diunsaturated-15-OH
subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

In addition, some 15-keto (i.e. having an oxo group at position 15 in place of the hydroxy group) prostaglandins and 13,14-dihydro-15-keto-prostaglandins are known as substances naturally produced by enzymatic actions during in vivo metabolism of primary PGs. 15-keto PGs have been disclosed in, for example, EP-A-0281239(corresponds to JP-A-104040/89), EP-A-0281480(corresponds to JP-A-52753/89), EP-A-0289349 (corresponds to JP-A-151552/89), EP-A-0453127(JP-A-58992/95) and EP-A-0690049 (corresponds to JP-A-48665/96). These cited references are herein incorporated by reference.

For example, when a primary type PG such as $PGE_2$ or $PGF_2\alpha$ which is a fatty acid derivative is instilled to the eyes at a stimulating amount which induces conjunctival hyperemia, lacrimation will occur simultaneously with the hyperemia. However, at an amount as low as that does not induce any conjunctival hyperemia, it is not known about the effect of the fatty acid derivatives including PGs on the tear secretion, basal tear secretion which is not affected by a stimulant, nor saliva secretion.

SUMMARY OF THE INVENTION

An object of the present invention is to provide a method for treatment of external secretion disorders, especially the method useful for treatment of at least one condition selected from hypolacrimation, dry-eye syndrome, hyposalivation and dry-mouth syndrome.

The present inventor found that at an amount as low as that does not induce any conjunctival hyperemia, a fatty acid derivative may improve hypolacrimation, improve basal tear secretion which is not affected by a stimulant, and improve the dry-eye conditions. In addition, the inventor also found that the fatty acid derivative might also improve hyposalivation, and improve dry-mouth conditions.

Therefore, the present invention provides a method for treatment of external secretion disorders, especially, for treatment of hypolacrimation, dry-eye syndrome, hyposalivation or dry-mouth syndrome, which comprises administering an effective amount of a fatty acid derivative to a subject in need of said treatment.

According to this invention, the term "fatty acid" includes not only the above mentioned linoleic acid, di-homo-γ-linolenic acid, arachidonic acid, α-linolenic acid, eicosapentaenoic acid (EPA) and docosahexaenoic acid (DHA), but also a compound comprising at least one carboxylic acid moiety irrespective to presence or absence of double bonds, a cyclic group or a substitute group, the number of the carbon atoms, position or number of the double bonds, or a modification on the chain. In addition, the fatty acid derivatives include not only the fatty acids as above but also prostaglandin like compounds which include $PG_s$ derived from said fatty acids, leukotriene like compounds, thromboxanes, hydroxyeicosatetraenoic acids, hydroperoxyeicosatetraenoic acids or their derivatives.

Furthermore, in the present invention, the fatty acid derivatives also include the compound which have at least —COOH or —CH$_2$OH or the functional derivatives (salts, esters, ethers, amides or the like) thereof at the terminal carbon atom, irrespective to presence or absence of double bonds, a cyclic group or a substitute group, the number of the carbon atoms, position or number of the double bonds, or a modification on the chain.

According to the present invention, the term "prostaglandin like compound" (hereinafter, referred as "PG like compound") includes any of derivatives or substituted derivatives of a compound having the prostanoic acid basic structure irrespective to the configuration of the 5-membered ring, number of double bonds in the α or ω chain, presence or absence of hydroxy and oxo groups or any other substituent, or any other modification. Since the PG like compound of the present invention may have an activity as an agonist for PG-receptor such as EP, FP, IP TP or DP receptor, the "PG like compound" of the present invention may include each compound having PG-receptor agonistic activity irrespective to their structure.

The nomenclature of the PG like compounds used herein is based on the numbering system of the prostanoic acid represented in the above formula (A).

The formula (A) shows a basic skeleton of the C-20, but the PG like compounds in the present invention are not limited to those having the same number of carbon atoms. I the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, the carbon atoms over position 20 are named as substituents. Stereochemistry of the compounds is the same as that of the above formula (A) unless otherwise specified.

In general, each of PGD, PGE and PGF represents a PG compound having hydroxy groups at positions 9 and/or 11, but in the present specification, they also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy compound.

As stated above, the nomenclature of the PG like compounds is based on the prostanoic acid skeleton. However, in case the compound has a similar partial construction as a prostaglandin, the abbreviation of "PG" may be used. Thus, a PG compound of which α-chain is extended by two carbon atoms; that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound, and a PG compound having 10 carbon atoms in the ω-chain is named as 20-ethyl-PG compound. These compounds, however, may also be named according to the IUPAC nomenclatures.

The PG like compounds used in the present invention may include any of PG derivatives. Accordingly, for example, a $PG_1$ compound having a double bond at 13-14 position and a hydroxy group at 15-position, a $PG_2$ compound having another double bond at 5-6 position, a $PG_3$ compound having further double bond at 17-18 position, a 15-keto-PG compound having an oxo group in place of the hydroxy group at the 15-position, a 15-dehydroxy-PG compound having a hydrogen atom in place of the hydroxy group at the 15-position, or either 13,14-dihydro-PG compound wherein the double bond at 13-14 position is single bond, or 13,14-didehydro-PG compound wherein the double bond at the 13-14 position is triple bond. Moreover, examples of substituted compounds and derivatives include a compound wherein the terminal carboxyl group in the α-chain of the above described compound is esterified, a physiologically acceptable salt thereof, a compound wherein the number of carbon atoms in the α- or ω-chain is decreased or increased, a compound having side chains (e.g., 1 to 3 carbon atoms) on α- or ω-chains, a compound having substituent(s) such as hydroxy, halogen, lower alkyl, hydroxy(lower)alkyl, and oxo, or double bond(s) on the five-membered ring, a compound having substituent(s), such as halogen, oxo, aryl and heterocyclic on the α-chain, a compound having substituents such as halogen, oxo, hydroxy, lower alkoxy, lower alkanoyloxy, cyclo(lower)alkyl, cyclo(lower)alkyloxy, aryl, aryloxy, heterocyclic and heterocyclic-oxy on the ω-chain, and a compound having substituent such as lower alkoxy, lower alkanoyloxy, cyclo(lower)alkyl, cyclo(lower)alkyloxy, aryl, aryloxy, heterocyclic and heterocyclic-oxy at the terminal of the ω-chain of which is shorter than that of normal prostanoic acid.

A preferred compound used in the present invention is represented by the formula (I):

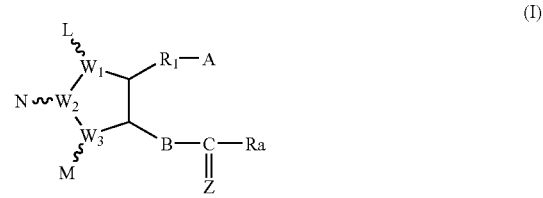

(I)

wherein $W_1$, $W_2$ and $W_3$ are carbon or oxygen atoms,

L, M and N are hydrogen, hydroxy, halogen, lower alkyl, hydroxy(lower)alkyl, or oxo, wherein at least one of L and M is a group other than hydrogen, and the five-membered ring may have at least one double bond;

A is —$CH_2OH$, —$COCH_2OH$, —COOH or its functional derivative;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$—, or —$CH_2$—C≡C—;

Z is

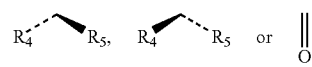

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a divalent saturated or unsaturated lower-medium aliphatic hydrocarbon residue, which is unsubstituted or substituted by halogen, oxo, hydroxy, lower alkyl, aryl or heterocyclic; and Ra is a saturated or unsaturated lower-medium aliphatic hydrocarbon residue, which is unsubstituted or substituted by halogen, oxo, lower alkyl, hydroxy, lower alkoxy, lower alkanoyloxy, cyclo(lower)alkyl, cyclo(lower)alkyloxy, aryl, aryloxy, heterocyclic or heterocyclic-oxy; cyclo(lower)alkyl; cyclo(lower)alkyloxy; aryl; aryloxy; heterocyclic; heterocyclic-oxy.

A group of particularly preferable compounds among the above described compounds is represented by the general formula (II):

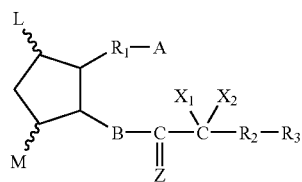

(II)

wherein L and M are hydrogen, hydroxy, halogen, lower alkyl, hydroxy(lower)alkyl, or oxo, wherein at least one of L and M is a group other than hydrogen, and the five-membered ring may have at least one double bond;

A is —CH$_2$OH, —COCH$_2$OH, —COOH or its functional derivative;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$—, or —CH$_2$—C≡C—;

Z is

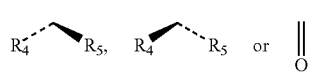

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$X_1$ and $X_2$ are hydrogen, lower alkyl, or halogen;

$R_1$ is a divalent saturated or unsaturated lower-medium aliphatic hydrocarbon residue, which is unsubstituted or substituted by halogen, oxo, hydroxy, lower alkyl, aryl or heterocyclic;

$R_2$ is a single bond or lower alkylene; and $R_3$ is lower alkyl, lower alkoxy, cyclo(lower)alkyl, cyclo(lower)alkyloxy, aryl, aryloxy, heterocyclic or heterocyclic-oxy.

Other preferred compound used in the present invention is represented by the formula (III):

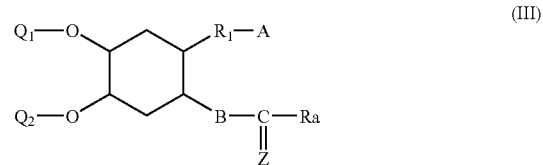

(III)

wherein $Q_1$ and $Q_2$ are hydrogen or lower alkyl, or $Q_1$ and $Q_2$ are linked together to form —(CH$_2$)$_n$— wherein n is 1, 2 or 0, and six-membered ring may have at least one double bond;

A is —CH$_2$OH, —COCH$_2$OH, —COOH or its functional derivative;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$—, or —CH$_2$—C≡C—;

Z is

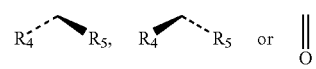

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a divalent saturated or unsaturated lower-medium aliphatic hydrocarbon residue, which is unsubstituted or substituted by halogen, oxo, hydroxy, lower alkyl, aryl or heterocyclic;

Ra is a saturated or unsaturated lower-medium aliphatic hydrocarbon residue, which is unsubstituted or substituted by halogen, oxo, hydroxy, alkyl, lower alkoxy, lower alkanoyloxy, cyclo(lower)alkyl, cyclo(lower)alkyloxy, aryl, aryloxy, heterocyclic or heterocyclic-oxy; cyclo(lower)alkyl; cyclo(lower)alkyloxy; aryl; aryloxy; heterocyclic; heterocyclic-oxy; and the six-membered ring may optionally have one or more double bonds and may optionally consist a conjugated system.

Among the above described compound (III), a preferable compound is benzene ring type compound in the six-membered ring.

In the above formula, the term "unsaturated" in the definitions for $R_1$ and $R_a$ is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions. Preferred unsaturated bonds are a double bond at position 2 and a double or triple bond at position 5.

The term "lower-medium aliphatic hydrocarbon" means a hydrocarbon having a straight or branched chain of 1 to 14 carbon atoms, wherein the side chain has preferably 1 to 3 carbon atoms. The preferred $R_1$ has 1 to 10, more preferably, 1 to 8 carbon atoms, and the preferred Ra has 1 to 10, more preferably, 1 to 8 carbon atoms.

The term "halogen" includes fluorine, chlorine, bromine, and iodine.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-o-wherein the lower alkyl is as described above.

The term "hydroxy(lower)alkyl" means an alkyl as described above, which is substituted by at least one hydroxy group, for example, hydroxymethyl, 1-hydroxyethyl, 2-hydroxyethyl, and 1-methyl-1-hydroxyethyl.

The term "lower alkanoyloxy" means a group represented by the formula RCO—O—, wherein RCO— is an acyl formed by oxidation of a lower alkyl as described above, for example, acetyl.

The term "lower cycloalkyl" means a group formed by cyclization of a lower alkyl group containing 3 or more carbon atoms as described above, for example, cyclopropyl, cyclobutyl, cyclopentyl, and cyclohexyl.

The term "cyclo(lower)alkyloxy" means a group represented by the formula cycloalkyl-O—, wherein cycloalkyl is described above.

The term "aryl" includes aromatic hydrocarbon rings (preferably monocyclic groups) which may be substituted, for example, phenyl, tolyl and xylyl. Examples of the substituent in this case include halogen, and halogen substituted lower alkyl group, wherein halogen atom and lower alkyl group are as described above.

The term "aryloxy" means a group represented by the formula ArO—, wherein Ar is an aryl group as described above.

The term "heterocyclic" includes mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, puryl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy" means a group represented by the formula HcO—, wherein Hc is a heterocyclic group as described above.

The term "functional derivative" of A includes salts (preferably pharmaceutically acceptable salts), ethers, esters, and amides.

Examples of suitable "pharmaceutically acceptable salts" include nontoxic salts which are commonly used, and salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy (lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidephenyl ester; and aryl(lower)alkyl esters such as benzyl ester, trityl ester, and benzhydryl ester. An example of amides includes mono- or di-lower alkyl amides such as methylamide, ethylamide, and dimethylamide; aryl amides such as anilide, and toluidide; and alkyl or aryl sulfonyl amides such as methylsulfonyl amide, ethylsulfonyl amide, and tolylsulfonyl amide.

Preferred examples of L and M include hydroxy and oxo, and especially, M is hydroxy and L is oxo which provide a 5-membered ring structure of, so called, PGE type.

Preferred examples of A-group include —COOH, and a pharmaceutically acceptable salt, an ester and an amide thereof.

In the formula (I) and (II), B is preferably —$CH_2$—$CH_2$— which provides the structure of so-called, 13,14-dihydro type.

In the formula (III), B is preferably single bond.

In the formula (I) and (II), Z is preferably =O which provides the structure of so-called keto-type.

In the formula (III), Z is preferably hydroxy.

Preferred examples of $X_1$, and $X_2$ are that at least one of them is halogen, more preferably, both of them are halogen, especially, fluorine that provides a structure of, so called 16,16-difluoro type.

Preferred $R_1$ is a hydrocarbon containing 2-10 carbon atoms, more preferably, 4-8 carbon atoms.

Examples of $R_1$ include, for example, the following groups:

—$CH_2$—$CH_2$—$CH_2$—$CH_2$—,
—$CH_2$—CH=CH—$CH_2$—,
—$CH_2$—C≡C—$CH_2$—,
—$CH_2$—$CH_2$—$CH_2$—$CH_2$—$CH_2$—,
—$CH_2$—CH=CH—$CH_2$—$CH_2$—,
—$CH_2$—C≡C—$CH_2$—$CH_2$—,
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—
—$CH_2$—C≡C—$CH_2$—$CH_2$—$CH_2$—,
—$CH_2$—$CH_2$—$CH_2$—$CH_2$—CH($CH_3$)—$CH_2$
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—,
—$CH_2$—$CH_2$—$CH_2$—$CH_2$—$CH_2$—$CH_2$—CH($CH_3$)—$CH_2$—,

Preferred Ra is a hydrocarbon containing 1-10 carbon atoms, more preferably, 1-8 carbon atoms and, especially, that having one or two side chains with one carbon atom.

The configuration of the ring and the α- and/or ω chains in the above formula (I) may be the same as or different from that of the primary PGs. However, the present invention also includes a mixture of a compound having a primary type configuration and a compound of a non-primary type configuration.

An example of the typical compound according to the present invention is 13,14-dihydro-15-keto-16-mono or difluoro PGE compound or a derivative thereof.

When a 15-keto-PG compound of the present invention has a saturated bond between positions 13 and 14, the compound may be in the keto-hemicetal equilibrium by formation of a hemiacetal between hydroxy at position 11 and keto at position 15.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the compounds used in the invention include both isomers. Further, while the compounds used in the invention may be represented by a structure formula or name based on keto-type regardless of the presence or absence of the isomers, it is to be noted that such structure or name does not intend to eliminate the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in EP-A 0281239 (corresponding to JP-A 64-052753), EP-A 0284180 (corresponding to JP-A 01-104040), EP-A 0289349 (corresponding to JP-A 01-151519), EP-A 0453127 (corresponding to JP-A 05-58992), EP-A 0690049 (corresponding to JP-A 08-48665) or U.S. Pat. No. 5,369,127. The references as above are herein incorporated by reference. Alternatively, these compounds may be prepared by a process analogous to that described herein or by any process known in the art.

As mentioned above, one of the characteristics of the PG like compounds of the present invention is a PG-receptor (ex. EP, FP, IP, TP and DP-receptor) agonist activity. Accordingly, the PG like compounds used in the present invention include any of compounds having a PG-receptor agonist activity, irrespective to their structure.

The above described fatty acid derivatives of the present invention are effective in treating external secretion disorders, especially in treating hypolacrimation including disorders in basal tear secretion, as well as in improving and treating of dry-eye conditions (i.e. decreased lacrimal fluid secretion and accompanying corneal disorders). Further, said compounds are also effective in improving hyposalivation, as well as in improving and treating of dry-mouth conditions. Therefore, the composition is useful for treatment of external secretion disorders, especially hypolacrimation including disorders in basal tear secretion and/or dry eye condition, or hyposalivation and/or dry-mouth conditions.

The term "treatment" or "treating" used herein refers to any means of control of a condition of a subject including prevention, cure, relief of the condition, and arrestation or relief of development of the condition.

The subjects who are intended to be treated by the method of the present invention are those suffered from external secretion disorder including xerosises such as dry-eye syndrome (xerophthalmia), dry-mouth syndrome (xerostomia), dry-nose syndrome (xeromycteria), dry-skin syndrome (xeroderma), dry-vagina syndrome (symptom of vaginal dryness); chronic pancreatitis, chronic gastritis, and chronic bronchitis due to the depression of external secretion. Especially, those with conditions which are likely to induce dry-eye syndrome include hypolacrimation, alacrima, xerophtalmia, Sjögren's syndrome, dry keratoconjunctivitis, Stevens-Johnson syndrome, ocular pemphigoid, marginal blepharitis, diabetes, post cataract operation and allergic conjunctivitis. In addition, those with dry-eye syndrome, which may be induced by aging, long term VDT operation, dryness of an air-conditioned room.

Systemic factors which may cause dry-mouth syndrome includes febrile disease, hypohydremia, endcrinopathy (myxedema, Basedow's disease, diabetes insipidus, etc.), metabolic disorders (diabetes, uremia, liver cirrhosis, etc.), deficiency of vitamin A or B, autoimmune diseases (Sjögren's syndrome, progressive scleroderma, etc.), anemia, bleeding, aging, various medications (sedatives, parasympatholytic drugs, antihistamines, etc.). In addition, topical factors may include sialadenitis, atrophy of salivary gland, sequela of radiotherapy, malformation ecodermal dysplasia, etc) and so forth.

The external secretion disorders means a state where abnormal external secretion (i.e. decrease or stop of the secretion), which may be caused by any etiology, is observed, especially the state with abnormal lacrimal fluid secretion including basal tear secretion, and abnormal salivation.

The method of the present invention may be effectuated by administering a composition comprising a fatty acid derivative as an active ingredient to the subject either orally or parenterally. The dosage form of the composition may be eye drops, ophthalmic ointment, sublingual tablets, troches, chewable tablets, collutoriums, sprays, ointments, powders, granules, tablets, capsules, suppository and vaginal suppository. Dosage forms for topical application, such as eyedrops, ophthalmic ointment, sublingual tablets and ointment are preferable. These dosage forms may be prepared according to any of conventional methods.

The composition used in the present invention may be admixed with an appropriate pharmaceutically acceptable additive. The additive is a compound which may be used together with the unsaturated fatty acid derivative of the invention and may include excipient, diluent, filler, solvent, lubricant, adjuvant, binder disintegrator, coating agent, cupsulating agent, ointment base, suppository base, aerosol base, emulsifier, dispersant, suspending agent, thickener, isotonic agent, buffering agent, analgesia, preservative, anti oxidant, corrigent, flavor, colorant, and functional agent (for example, cyclodextrin and biodegradable polymer). The additive may be selected based on any of reference books on pharmaceuticals.

The composition used in the present invention may further be admixed with any of pharmaceutically active agents in so far as said agent is compatible with the purpose of the present invention.

In the present invention, the "effective amount" of a fatty acid derivative may vary depending on the kind of the fatty acid used, the condition to be treated, age and body weight of the patient, dosage form, duration of the treatment, desired therapeutic effect and so on. For example, when the composition to be used in the treatment is formulated as eyedrops, a dosage form containing 0.000001-10.0 wt %, preferably 0.00001-1.0 wt % of the fatty acid derivative may be administered several drops per one eye, preferably 1-4 drops, several times per day, preferably, 1-6 times per day. When it is formulated as a sublingual tablet, a dosage form containing 0.000001-10.0 wt %, preferably 0.00001-1.0 wt % of the fatty acid derivative may be administered in the oral cavity several times, preferably 1-6 times per day. Further, when it is formulated as an ointment, topical administration of a dosage form containing 0.000001-10.0 wt %, preferably 0.00001-1.0 wt % of the fatty acid derivative for several times, preferably, 1-6 times per day may provide an enough effect.

EXAMPLES

The present invention will be illustrated in more detail by way of the following examples. These examples should not be used as any limitation of the present invention.

Test Example 1

Effect on Whole Tear Secretion of Normal Rabbits (1) Test Animals

Male Japanese albino rabbits (Std:JW/CSK) were used.

(2) Method of Administration

Ophthalmic solution comprising 0.001% of 13,14-dihydro-15-keto-16,16-difluoro-$PGE_1$ as an active ingredient of the present invention was prepared and used as a test composition. As a control, the vehicle of said solution without the active ingredient was used.

Each of the compositions was instilled singly to eight eyes at the amount of 30 μl/eye. After the administration, the time course of the tear secretion change was examined according to the following method.

(3) Examination

Whole Tear Secretion

Before (0 hour) and 0.5, 2, 4, and 6 hours after the instillation, the whole tear secretion was determined.

Under no anesthetization, one edge of the Schirmer's test strip (Showa Yakuhin Kako Co., Ltd., Lot No. 70080) was inserted into the conjunctival sac of the each test animal. One minute after, the strip was removed and the length of the moisted part was read from the scale provided on the strip to determine the amount of whole tear secretion.

(4) Result

The result of the whole tear secretion test is shown in the Table 1. No stimulating response, such as rubor in the front of the eye was observed after the administration in both of the test animals and the control animals.

These data are shown simultaneously with the statistical analysis.

TABLE 1

| | number of the eyes tested | time (hr) | whole tear secretion (mm/min.) |
|---|---|---|---|
| Control group | 8 | before the administration | 5.5 ± 0.3 |
| | 8 | 0.5 | 8.1 ± 0.7 |
| | 8 | 2 | 8.3 ± 0.8 |
| | 8 | 4 | 7.3 ± 0.7 |
| | 8 | 6 | 7.1 ± 0.7 |
| test group 0.001% | 8 | before the administration | 5.3 ± 0.2 |
| | 8 | 0.5 | 17.0 ± 0.5## |
| | 8 | 2 | 14.1 ± 0.5## |
| | 8 | 4 | 11.7 ± 0.6## |
| | 8 | 6 | 10.5 ± 1.0# |

$p < 0.05$ ##$p < 0.01$: comparison with the value at the corresponding time of the control group (Student's-t test).

According to the above result, the test group comprising the compound of the present invention as an active ingredient caused a significant increase of the amount of whole tear secretion at a dose which does not induce any stimulating response such as rubor in the front of the eye. Therefore, the compound of the present invention was revealed to have an activity to increase the amount of tear secretion without any stimulating response.

Test Example 2

Effect of the Compound on Decreased Whole Tear Secretion, Decreased Basal Tear Secretion and Keratoepithelial Lesion in Rabbit Dry-eye Syndrome Model, which was Induced by Trigeminal Denervation (1) Test Animals Fifteen male Japanese albino rabbits (Std:JW/CSK) were used.

(2) Generating Rabbit Dry-eye Syndrome Model by Trigeminal Denervation.

i) Operational Procedure

Urethane (ALDRICH) was administered i.p. at the dose of 1 g/kg to the rabbits of which occipital hair had been shaved.

After disinfecting of the shaved area, midline incision of the skin was made from the frontal bone to the ear root, and the muscular tissue around the periosteum, temporal bone and manidibular articular process were detached. After the detachment, a hole of 2×1.5 cm in size was made in the bone from the parietal medial region to the temporal region by means of the bone drill (URAWA KOGYO Co., Ltd. MINITOR C-130) under the surgical microscope (KONAN CAMERA R&I Inc., PMO-50). Then, the dura was detached from the cranial bone while cotton bud was kept inserted between the temporal bone and the dura. After the detachment was made up to the cranial base, detachment was further made toward the medial border of the petrous part of temporal bone in the carnial cavity, to find the trigeminal nerve in the petrous part. Then, the dura of about 1 to 2 mm on the nasal side of the semilunar ganglion was incised. After the incision, the two branches of nerve fascicle, i.e. the first branch (ocular nerve) of the trigeminal nerve and the second branch (maxillary nerve) were pulled laterally and cut with corneoscleral scissors. Immediately after the operation, miosis of the ipsilateral eye was confirmed and then the cotton kept inserted was removed, and the skin at the head was closed with suture. After the operation, an antibiotic (MYCILLIN SQL® Meiji) was administered i.m. at the dose of 0.1 ml/kg.

The trigeminal denervation was made only on the left eye side, while on the right eye side, no trigeminal denervation nor sham operation was made.

After the operation, animals in stable state and showed decreased whole tear secretion, decreased basal tear secretion, and keratoepithelial lesion were subjected to the following test.

(3) Method of Administration.

13,14-dihydro-15-keto-16,16-difluoro-$PGE_1$ was used as an active ingredient of the present invention to prepare test eyedrops containing 0.0001% and 0.001% of the compound. As a control, the vehicle of the eyedrops without the active ingredient was used.

Each of the compositions was instilled to the eyes everyday at the volume of 30 μl/eye two times a day (at 10:00 and 18:00) for two weeks. Five eyes per each of the test groups and the control group were treated and then examined for the whole tear secretion, the basal tear secretion and the keratoepithelial lesion as follows.

(4) Examination i) Whole Tear Secretion (Schirmer's Test)

Before the start of the instillation (week 0), and 1, 2, and 3 weeks after the start, the whole tear secretion was measured two hours after the first instillation on the day of examination.

Under no anesthetization, one edge of the Schirmer's test strip (Showa Yakuhin Kako Co., Ltd., Lot No. 70080) was inserted into the conjunctival sac of each test animal. One minute after, the strip was removed and the length of the moistened part was read from the scale provided on the strip to determine the amount of whole tear secretion.

ii) Basal Tear Secretion

Before the start of the instillation (week 0), and 1, 2, and 3 weeks after the start, the basal tear secretion was measured 2 hours after the 1st instillation on the day of the examination.

Keratoconjunctiva was anesthetized by instillation of 4% lidocaine (Xylocalne® 4% for ophthalmic solution; Fujisawa Pharmaceutical Co., Ltd.), the eye drops and the tear around the eyelid were wiped off about 5 minutes after and loss of keratoconjunctival esthesia was confirmed with the Cochet-Bonnet type esthesiometer. Then, one edge of the Shirmer's test strip was inserted into the conjunctival sac and kept there for 5 minutes. The length of the moistened part was read from the scale on the strip.

The basal tear secretion was expressed by mean value per minute calculated from the 4-minutes value obtained by subtracting the initial 1-minute value from the 5-minutes Sirmer's test, so that the spontaneous volume of the tear retained in the conjunctival sac might be excluded.

iii) Keratoepithelial Lesion

Before the start of instillation (week 0) and 1, 2, and 3 weeks after the start, the keratoepithelial lesion was evaluated two hours after the first instillation on the day of examination.

Each animal was placed in a stainless steel fixator, and given instillation of 50 μl of the mixture of 1% rose bengal and 1% fluorescein to stain their keratoconjunctival epithelium. Stained area, i.e. the abnormal area on the epithelium was evaluated according to the criteria shown in the Table 2.

TABLE 2

| Scores | Stained area of the keratoconjunctiva |
|---|---|
| 0 | None |
| 0.5 | only a part was stained slightly |
| 1 | the area was less than ¼ |
| 2 | the area was more than ¼ and less than ½ |
| 3 | the area was more than ½ and less than ¾ |
| 4 | the area was more than ¾ |

(5) Results

The result of the whole tear secretion is shown in the Table 3, that of the basal tear secretion is shown in the Table 4, and that of the keratoepithelial lesion is shown in the Table 5. Statistical analysis is also shown with the data.

TABLE 3

| | number of eyes | time (weeks) | whole tear secretion (mm/min.) |
|---|---|---|---|
| before the operation | 15 | — | 5.23 ± 0.33 |
| after the operation | 15 | — | 3.10 ± 0.28** |
| control group | 5 | before administration | 3.10 ± 0.40** |
| | 5 | 1 | 4.40 ± 1.21 |
| | 5 | 2 | 3.80 ± 0.64* |
| | 5 | 3 | 3.90 ± 0.90 |
| test group 0.0001% | 5 | before administration | 3.00 ± 0.61** |
| | 5 | 1 | 7.10 ± 0.51**++ |
| | 5 | 2 | 6.60 ± 0.37*##++ |
| | 5 | 3 | 6.30 ± 0.68++ |
| test group 0.001% | 5 | before administration | 3.20 ± 0.51** |
| | 5 | 1 | 11.20 ± 0.51**##++ |
| | 5 | 2 | 10.50 ± 0.57**##++ |
| | 5 | 3 | 9.90 ± 0.81**##++ |

$*p < 0.05$ $**p < 0.01$: comparison with the value before the operation(student's-t test)
$^+p < 0.05$ $^{++}p < 0.01$: comparison with the value at the corresponding time in the control group(Student's-t test)
$^\#p < 0.05$ $^{\#\#}p < 0.01$: comparison with the value of time 0 (before administration) in each treatment group.

TABLE 4

| | number of eyes | time (weeks) | basal tear secretion (mm/min.) |
|---|---|---|---|
| before the operation | 15 | — | 1.45 ± 0.10 |
| after the operation | 15 | — | 0.43 ± 0.05[**] |
| control group | 5 | before administration | 0.43 ± 0.10** |
| | 5 | 1 | 0.88 ± 0.21* |
| | 5 | 2 | 0.73 ± 0.22** |
| | 5 | 3 | 0.73 ± 0.18** |
| test group 0.0001% | 5 | before administration | 0.43 ± 0.06[**] |
| | 5 | 1 | 1.53 ± 0.26[+] |
| | 5 | 2 | 1.60 ± 0.11**++ |
| | 5 | 3 | 1.48 ± 0.17#[++] |
| test group 0.001% | 5 | before administration | 0.43 ± 0.08** |
| | 5 | 1 | 2.00 ± 0.12*##++ |
| | 5 | 2 | 2.00 ± 0.18*##++ |
| | 5 | 3 | 2.00 ± 0.14*##++ |

[**]$p < 0.01$: comparison with the value before the operation (Aspin-Welch test)
$*p < 0.05$ $**p < 0.01$: comparison with the value before the operation in each group(student's-t test)
$^{++}p < 0.01$: comparison with the value at the corresponding time in the control group(Student's t-test)
[+]$p < 0.05$ [++]$p < 0.01$: comparison with the value at the corresponding time in the control group(Aspin-Welch test)
$^\#p < 0.05$ $^{\#\#}p < 0.01$: comparison with the value of time 0 (before administration) in each test group (Student's-t test).

TABLE 5

| | number of eyes | time (weeks) | Keratoepithelial lesion (score) |
|---|---|---|---|
| before the operation | 15 | — | 0.07 ± 0.05 |
| after the operation | 15 | — | 2.93 ± 0.15[**] |
| control group | 5 | before administration | 2.80 ± 0.20[**] |
| | 5 | 1 | 1.90 ± 0.51[**] |
| | 5 | 2 | 1.60 ± 0.58[**] |
| | 5 | 3 | 1.50 ± 0.32[**]++ |
| test group 0.0001% | 5 | before administration | 3.00 ± 0.32[**] |
| | 5 | 1 | 1.00 ± 0.27[*]++ |
| | 5 | 2 | 0.50 ± 0.16[*]++ |
| | 5 | 3 | 0.40 ± 0.19#++ |
| test group 0.001% | 5 | before administration | 3.00 ± 0.32[**] |
| | 5 | 1 | 0.70 ± 0.34++ |
| | 5 | 2 | 0.10 ± 0.10[++] |
| | 5 | 3 | 0.10 ± 0.10[##][++] |

[*]$p < 0.05$ [**]$p < 0.01$: comparison with the value before the operation (Aspin-Welch test)
$^{++}p < 0.01$: comparison with the value before the operation in each group (student's-t test)
[++]$p < 0.01$: comparison with the value at the corresponding time in the control group(Aspin-Welch test)
[##] $p < 0.01$: comparison with the value of time 0 (before administration) in each test group (Aspin-Welch test).

Based on the above results, the test group comprising the compound of the present invention as an active ingredient improved the decreased whole tear secretion and basal tear secretion as well as keratoconjunctival lesion accompanied by the decrease of the tear secretion observed in the dry-eye syndrome model animals. Therefore, the composition of the present invention is appear to be useful for treatment of hypolacrimation including disorders in basal tear secretion as well as dry-eye conditions i.e. hypolacrimation and accompanying keratoconjunctival lesion.

Test Example 3

Exaltation of Salivation

The effect of the composition of the present invention on salivary secretion was determined.

(1) Test Animals
Male and female rats (Crj:CD strain) were used. Each of the test and control groups contains 16 animals.

(2) Method of Administration
13,14-dihydro-15-keto-16,16-difuloro-$PGE_1$ was used as an active ingredient of the present invention to prepare test solution containing 0.2 mg/ml of the compound.
5 ml/kg of the solution (1 mg/kg of the compound) was forcedly administered orally once a day. For the animals of control group, 5 ml/kg of the vehicle without the active ingredient was administrated once a day. The administration was continued for four weeks.

(3) Examination
The amount of the saliva of the test group and control group was evaluated visually everyday.

(4) Result
In the group of the animals administered with the fatty acid derivative of the present invention, exaltation of saliva was observed in 8 of 16 rats on the 10th day after the start of the administration, and after that, the number of the rats with salivary exaltation was increased time dependently. Subsequent to the 22nd day after the start, each of 16 rats administrated with the composition showed salivary exaltation. Whereas, in the control group, all animals kept the normal salivary secretion over the whole administration term.

Test Example 4

Exaltation of Salivation

The effect of the composition of the present invention on salivary secretion was determined.

(1) Test Animals

Male rats (SD strain) were used. Each of the test and control groups contains 8 animals.

(2) Method of Administration 13,14-dihydro-15-keto-16,16-difuloro-$PGE_1$ was used as an active ingredient of the present invention to prepare test solution containing 0.2 mg/ml of the compound.

5 ml/kg of the solution (1.0 mg/kg of the compound) was forcedly administrated orally once a day. For the animals f control group, 5 ml/kg of vehicle without the active ingredient was administrated once a day. The administration was continued for 10 days.

(3) Examination

The amount of the saliva of the test group and control group was measured one hour after the administration on 10th day. The edge of a paper filter (Schirmer's test strip, Showa Yakuhin Kako Co., Ltd.) was inserted between lower gingiva and mandibula. Three minutes after, the paper filter was removed and the weight of the saliva was calculated by the following formula.

weight of saliva=(the weight of paper filter including saliva)−(weight of only paper filter)

(4) Result

The result of the salivary secretion is shown in the table 6.

TABLE 6

| | Number of animals | Salivary weight (mg, mean ± S.E.) |
|---|---|---|
| Control group | 8 | 4.6 ± 0.9 |
| Test group | 8 | 18.1 ± 5.6* |

*$P < 0.05$, compared with control group (U-test of Mann-Whitney)

In the group of the animals administered with the fatty acid derivative of the present invention, salivary secretion was significantly increased compared with that of the control group.

Test Example 5

Effect on Whole Tear Secretion of Normal Rabbits (1) Test Animals

Male Japanese albino rabbits were used.

(2) Method of Administration

Ophthalmic solution comprising an active ingredient of the present invention was prepared and used as a test composition.

Each of the compositions was instilled to the eye singly at the amount of 30 μl/eye.

(3) Examination

Amount of the Tear Secretion

Before (0 hour) and 2 hours after the instillation, the whole tear secretion was determined.

Under no anesthetization, one edge of the Schirmer's test strip (Showa Yakuhin Kako Co., Ltd.) was inserted into the conjunctival sac of the each test animal. One minute after, the strip was removed and the length of the moisted part was read from the scale provided on the strip to determine the amount of whole tear secretion.

The rate (%) of increased amount of whole tear secretion was calculated at the 2 hours after the instillation compared with the before (0 hour).

(4) Result

10 The result of the whole tear secretion test is shown in the Table 7. In addition to the data in the table, no stimulating response, such as rubor, in the front of the eye was observed after the administration of test compounds.

TABLE 7

| Test compound | Concentration of the test compound | Number of the eyes tested | Rate of the increased whole tear secretion (%) |
|---|---|---|---|
| Compound 1 | 30 μg/ml | 4 | 40.7 |
| Compound 2 | 10 μg/ml | 4 | 52.5 |
| Compound 3 | 10 μg/ml | 4 | 52.0 |
| Compound 4 | 3 ug/ml | 4 | 61.8 |
| Compound 5 | 3 ug/ml | 4 | 43.5 |
| Compound 6 | 100 μg/ml | 4 | 44.0 |
| Compound 7 | 2000 μg/ml | 4 | 56.9 |
| Compound 8 | 1 μg/ml | 4 | 24.8 |

Compound 1: 15-dehydroxy-13,14-dihydro-14,15-dehydro-16keto-17,17-difluoro-PGE1-methyl ester
Compound 2: 13,14-dihydro-15-keto-16,16-difluoro-20-ethyl-$PGE_1$
Compound 3: 2-decarboxy-2-(2-carboxyethyl)-13,14-dihydro difluoro-PGE1
Compound 4: 13,14-dihydro-15-keto-16,16-difluoro-$PGF_{2\alpha}$-Methyl ester
Compound 5: 11-dehydroxy-13,14-dihydro-15-keto-16,16-difluoro-$PGE_1$
Compound 6: 13,14-dihydro-15-keto-16,16-difluoro-$PGE_1$
Compound 7: 2-decarboxy-2-(2-carboxyethyl)-13,14-dihydro 15-keto-16,16-difluoro-20-ethyl-$PGE_1$-isopropyl ester
Compound 8: 13,14-dihydro-15-keto-16,16-difluoro-$PGE_2$

What is claimed is:

1. 11-dehydroxy-13,14-dihydro-15-keto-16,16-difluoro-$PGE_1$, or a salt, ether, ester or amide thereof.

2. 11-dehydroxy-13,14-dihydro-15-keto-16,16-difluoro-$PGE_1$.

* * * * *